United States Patent
Bunge et al.

(10) Patent No.: US 11,350,855 B2
(45) Date of Patent: Jun. 7, 2022

(54) SENSOR SYSTEM, METHOD AND CROSS-LINKED HYDROGEL FOR DETECTING THE PRESENCE OR CONCENTRATION OF ANALYTES

(71) Applicant: BIOTRONIK SE & CO. KG, Berlin (DE)

(72) Inventors: Andreas Bunge, Leipzig (DE); Henning Ebert, Berlin (DE); Olaf Skerl, Bad Doberan (DE); Alexander Borck, Heidesee (DE)

(73) Assignee: BIOTRONIK SE & Co. KG, Berlin (DE)

( * ) Notice: Subject to any disclaimer, the term of this patent is extended or adjusted under 35 U.S.C. 154(b) by 523 days.

(21) Appl. No.: 15/831,983

(22) Filed: Dec. 5, 2017

(65) Prior Publication Data
US 2018/0153453 A1   Jun. 7, 2018

(30) Foreign Application Priority Data
Dec. 5, 2016   (EP) .................................... 16202111

(51) Int. Cl.
*A61B 5/145* (2006.01)
*G01N 1/38* (2006.01)
(Continued)

(52) U.S. Cl.
CPC ........ *A61B 5/14532* (2013.01); *A61B 5/0031* (2013.01); *A61B 5/14546* (2013.01);
(Continued)

(58) Field of Classification Search
CPC ........ A61B 5/14532; A61B 2562/0247; A61B 2562/168
See application file for complete search history.

(56) References Cited

U.S. PATENT DOCUMENTS

| | | | |
|---|---|---|---|
| 5,854,078 A | 12/1998 | Asher et al. | |
| 5,898,004 A | 4/1999 | Asher et al. | |

(Continued)

FOREIGN PATENT DOCUMENTS

| | | |
|---|---|---|
| WO | 9819787 A1 | 5/1998 |
| WO | 9841859 A1 | 9/1998 |
| WO | 03031945 A1 | 4/2003 |

OTHER PUBLICATIONS

Xiao-Jie Ju, et al.; "A Novel Thermoresponsive Hydrogel with Ion-Recognition Property through Supramolecular Host-Guest Complexation"; The Journal of Physical Chemistry B; Jan. 8, 2008; pp. 1112-1118; vol. 112; © 2008 American Chemical Society; DOI: 10.1021/jp709746w.

(Continued)

*Primary Examiner* — Puya Agahi
(74) *Attorney, Agent, or Firm* — Laurence A. Greenberg; Werner H. Stemer; Ralph E. Locher (57) ABSTRACT

A sensor system detects a presence or concentration of an analyte in a medium. The sensor system contains a sensor having a sensor head with a chamber. The sensor head has a permeable area through which the analyte can pass into the chamber when the sensor head contacts the medium. A cross-linked hydrogel fills the chamber, the hydrogel is configured to undergo a change in volume when contacting the analyte passed into the chamber which leads to a change in pressure in the chamber. A pressure sensor is configured to measure the pressure in the chamber for detecting the presence or concentration of the analyte.

12 Claims, 9 Drawing Sheets

(51) Int. Cl.

| | | |
|---|---|---|
| C08L 33/26 | (2006.01) | |
| G01N 33/543 | (2006.01) | |
| G01N 33/53 | (2006.01) | |
| B01J 13/00 | (2006.01) | |
| G01N 7/10 | (2006.01) | |
| G01N 15/06 | (2006.01) | |
| G01N 27/12 | (2006.01) | |
| A61B 5/1473 | (2006.01) | |
| G01N 33/49 | (2006.01) | |
| A61B 5/00 | (2006.01) | |
| A61B 5/1495 | (2006.01) | |
| G01N 15/00 | (2006.01) | |

(52) U.S. Cl.
CPC ....... *A61B 5/14735* (2013.01); *B01J 13/0065* (2013.01); *C08L 33/26* (2013.01); *G01L 1/38* (2013.01); *G01N 7/10* (2013.01); *G01N 15/06* (2013.01); *G01N 27/126* (2013.01); *G01N 33/49* (2013.01); *G01N 33/5308* (2013.01); *G01N 33/54366* (2013.01); *A61B 5/1495* (2013.01); *A61B 5/6867* (2013.01); *A61B 2560/0223* (2013.01); *A61B 2560/0247* (2013.01); *A61B 2562/0247* (2013.01); *A61B 2562/168* (2013.01); *G01N 2015/0065* (2013.01)

(56) References Cited

U.S. PATENT DOCUMENTS

| | | | |
|---|---|---|---|
| 6,187,599 B1 | 2/2001 | Asher et al. | |
| 6,475,750 B1 | 11/2002 | Han et al. | |
| 6,544,800 B2 | 4/2003 | Asher | |
| 6,753,191 B2 | 6/2004 | Asher et al. | |
| 7,105,352 B2 | 9/2006 | Asher et al. | |
| 8,323,193 B2 * | 12/2012 | Skerl | A61B 5/14532 600/309 |
| 2002/0042065 A1 * | 4/2002 | Han | A61B 5/14532 435/6.11 |
| 2010/0256465 A1 * | 10/2010 | Bernstein | A61B 5/685 600/309 |
| 2010/0285094 A1 * | 11/2010 | Gupta | A61L 31/145 424/429 |
| 2012/0150006 A1 * | 6/2012 | Lavanant | C12Q 1/006 600/347 |
| 2016/0109370 A1 | 4/2016 | Ku et al. | |
| 2016/0252505 A1 * | 9/2016 | Braun | G01N 33/544 436/501 |
| 2016/0349162 A1 * | 12/2016 | Ebert | G01N 33/49 |
| 2017/0027482 A1 * | 2/2017 | Zilberstein | A61B 5/14546 |

OTHER PUBLICATIONS

Volker Schulz, et al.; "A Closed-Loop Hydrogel-Based Chemical Sensor"; IEEE Sensors Journal; Mar. 2013; pp. 994-1002; vol. 13; IEEE; DOI: 10.1109/JSEN.2012.2227709.

Kangfa Deng, et al.; "Design, simulation and characterization of hydrogel-based thermal actuators"; Sensors and Actuators B: Chemical; Nov. 2016; pp. 900-908; vol. 236, Elsevier; DOI: 10.1016/j.snb.2016.03.060.

Kangfa Deng, et al.; "Force-compensated hydrogel-based pH sensor"; Active and Passive Smart Structures and Integrated Systems 2015 , Proc. of SPIE; vol. 9431; DOI: 10.1117/12.2084171.

* cited by examiner

SENSOR SYSTEM, METHOD AND CROSS-LINKED HYDROGEL FOR DETECTING THE PRESENCE OR CONCENTRATION OF ANALYTES

CROSS-REFERENCE TO RELATED APPLICATION

This application claims the benefit, under 35 U.S.C. § 119, of European patent application EP 16202111.7, filed Dec. 5, 2016; the prior application is herewith incorporated by reference in its entirety.

BACKGROUND OF THE INVENTION

Field of the Invention

The invention relates to a sensor system, method and hydrogel for detecting the presence or concentration of an analyte.

Such sensors for detecting the presence/concentration of an analyte in a fluid medium can be based on polymers such as hydrogels which react to a stimulus, here the presence/specific concentration of an analyte with pronounced volume changes, for instance due to incorporation or release of water molecules.

For realizing such a material and for detecting the presence, particularly concentration of an analyte, hydrogels are typically modified to comprise selective responsive components which are able to selectively bind an analyte.

In such a hydrogel being maintained at a defined temperature, the binding of the analyte to the hydrogel disturbs the balance between the tendency to capture water and to release water from the hydrogel. In case of electrolyte-sensitive hydrogels containing crown ether, the amount of bound water per crown ether differs significantly for the free configuration and complex containing the metal ion (analyte). Therefore, actually small changes in analyte concentration may lead to large changes of the swelling level (i.e. water content and volume). These effects can be drastically amplified when the hydrogel exhibits a critical volume phase transition at a so called lower critical solution temperature (LCST), at which the volume of the hydrogel changes abruptly from the swollen to the shrunken state (and vice versa).

Figure 1:
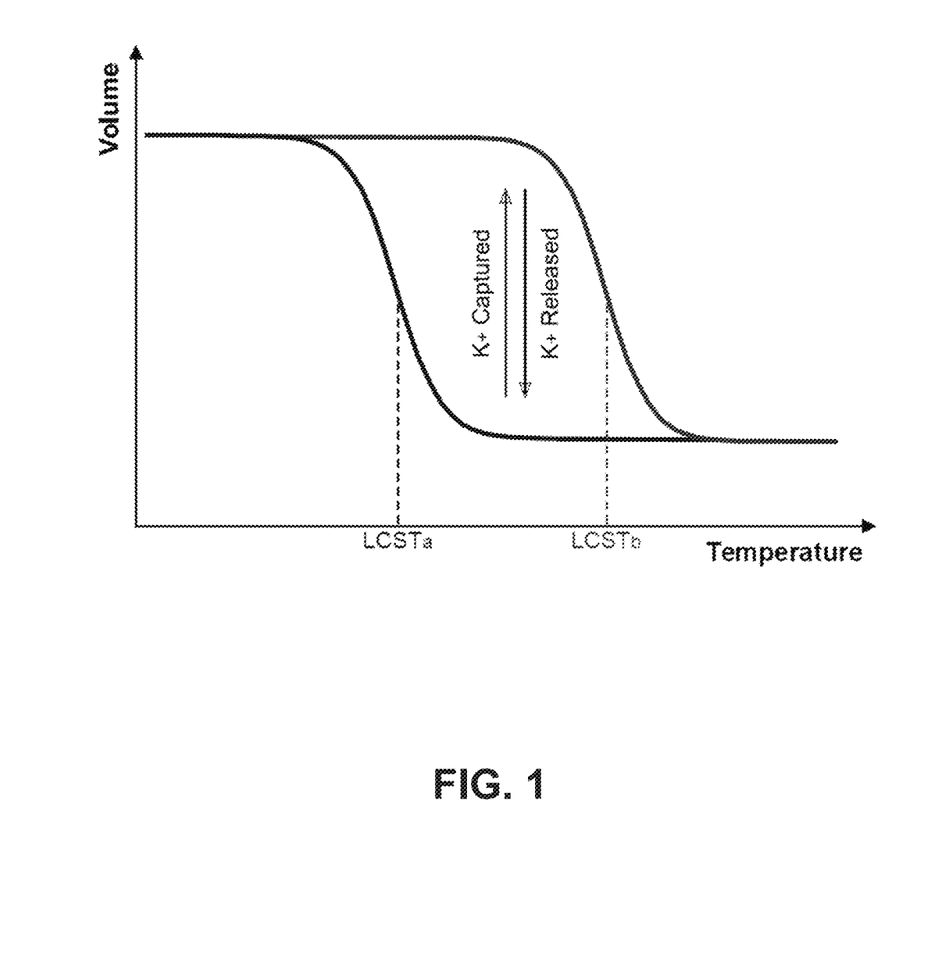
FIG. 1 is a graph showing a volume transition of a hydrogel in isobaric conditions.

As indicated in FIG. 1, the transition temperature LCST, here in case of a hydrogel sensitive to $K^+$ is decreased due to capture of $K^+$ in a 2:1 crown ether complex. At a constant temperature a reversible release of water and a decrease in volume occurs. In case the potassium concentration is lowered, potassium is removed from the crown ether and water is received in the hydrogel resulting in an increasing volume. It is known, that under these conditions, hydrogels are only sensitive to an analyte in a rather narrow temperature interval around LCST (here between $LCST_a$ and $LCST_b$). This can be explained by the observation that only in this interval the volume-temperature curve contains a significant slope. Due to the detection of the analyte the shift of this curve thus only results in a vertical distance at these temperatures which corresponds to a change in volume. In the remaining temperature regions (in case of Poly(N-isopropylacrylamid)(PNIPAAm) below 30° C. and above 33° C.) the curve does not comprise a significant slope, such that the shift of the curve due to potassium does not result in a significant change of volume of the hydrogel.

Further, particularly, international patent disclosure WO 98/19787 (corresponding to U.S. Pat. Nos. 7,105,352, 6,753, 191, 6,544,800, 6,187,599, 5,898,004 and 5,854,078) discloses a sensor device composed of a crystalline colloidal array (CCA) polymerized in a hydrogel. The hydrogels are characterized as being capable of shrinking and swelling in response to specific stimuli applied thereto which changes the embedded lattice structure of the CCA which is optically monitored.

In the state of the art, particularly in WO 98/19787, hydrogels are usually considered at constant (ambient) pressure and changes of the properties of the respective hydrogel are often characterized using gravimetric or optical methods. However, under isobaric conditions, as described above, the sensitivity of the hydrogel to the respective analyte is limited to a small temperature region.

SUMMARY OF THE INVENTION

Thus, the problem to be solved by the present invention is to provide a sensor system that avoids the above-stated disadvantage of a small useable temperature interval.

This problem is solved by a sensor system having the features of the main patent claim.

Further aspects of the present invention are described below. Specific embodiments of the sensor system according to invention are stated in the sub claims and are also described below.

With the foregoing and other objects in view there is provided, in accordance with the invention, a sensor system for detecting the presence or concentration of an analyte in a medium is disclosed. The sensor system containing a sensor having a sensor head comprising a chamber, which sensor head comprises a permeable area through which the analyte can pass into the chamber when the sensor head contacts the medium. A cross-linked hydrogel fills the chamber, which hydrogel is configured to undergo a change in volume (e.g. the hydrogen swells or shrinks) when contacting the analyte passed into the volume which leads to a change in pressure in the chamber (particularly due to the isochoric state of the hydrogel in said chamber). A pressure sensor is provided (particularly arranged in the volume) that is configured to measure the pressure in the chamber for detecting the presence or concentration of the analyte.

Particularly, in the framework of the present invention, a cross-link is an (e.g. covalent) bond that links one polymer chain to another. A cross-linked hydrogel is a hydrogel comprising a plurality of polymer chains, wherein each of the polymer chain comprises at least one cross-link, particularly a plurality of cross-links, to another polymer chain. Macroscopically, cross-linking has the effect on polymers that they are no longer soluble in solvents, and indeed exhibit swelling upon solvent uptake.

Particularly, the sensor system can be configured to conduct determining the concentration in a continuous fashion or merely at specific points in time (e.g. at regular intervals).

Particularly, in an embodiment said permeable area can comprise a membrane or grid that is permeable for the analyte, but not for the hydrogel residing in the chamber, wherein the area forms a counter bearing for the hydrogel so that a pressure can build up in the chamber when the hydrogel tends to swell in the chamber due to a change in concentration of the analyte in the chamber of the sensor head.

Surprisingly, it has been found that using a cross-linked hydrogel in isochoric conditions (e.g. in the chamber of the sensor head) significantly increases the temperature interval in which measurements can be performed. This is due to the surprising fact that the hydrogel comprises essentially a linear dependency of the measures pressure over a wide range of temperatures below LCST.

Furthermore, the cross-linked hydrogel comprises a sufficient stability that allows loading the hydrogel in the isochoric chamber with a pressure. Furthermore, such a cross-linked hydrogel is much less likely to escape from the chamber of the sensor head than a linear hydrogel/polymer, which are not suited for these kinds of pressure measurements.

Due to the fact that measurements can now be performed over a much wider range of practical temperatures complex mathematical procedures to compensate of a strong temperature dependence of the respective measurement or the need to keep the temperature constant upon measuring can be avoided. Moreover, keeping the temperature constant is hardly possible when the sensor head is implanted into a patient that exhibits a varying body temperature (e.g. due to a fever etc.)

Particularly. according to an embodiment the cross-linked hydrogel is a thermo-responsive polymer that comprises a lower critical solution temperature (LCST), i.e. a critical temperature below which the components of a mixture, here a polymer and water, are miscible for all compositions, which LCST decreases when the analyte bonds to the hydrogel and which increases when the analyte is released from the hydrogel, wherein below the LCST the measured pressure depends linearly and/or mildly quadratically on the temperature of the hydrogel. This means that the sensor comprises essentially a constant sensitivity for the analyte over a relatively broad range of temperatures below LCST due to the essentially linear and/or mildly quadratically dependence of the pressure signal on temperature.

At the LCST the volume of the hydrogel changes abruptly with temperature from a swollen to a shrunken state (and vice versa). Increasing the temperature of a swollen hydrogel above the LCST leads to a decreased efficiency of the hydrogen bonds between the polymer and water which finally does not suffice to keep the polymer in the solution. Thus, a phase separation occurs, wherein water is released from the polymer resulting in two phases: a polymer-enriched phase and an aqueous phase that does not comprise the polymer. Alternatively, also hydrogels having an upper critical solution temperature (UCST) or hydrogels exhibiting both, an LCST and a UCST may be used in the sensor system according to the present invention.

Further, according to a preferred embodiment of the present invention, the hydrogel comprises a plurality of a responsive component (e.g. compound), wherein the respective responsive component is responsive to the analyte such that the volume of the hydrogel tends to decrease when the respective responsive compound binds (non-covalently) to a specific analyte such that the pressure in the chamber decreases, and wherein the volume of the hydrogel tends to increases when a specific analyte is released from the respective responsive compound.

Further, according to a preferred embodiment of the present invention, the responsive component (e.g. compound) comprises one of:
a crown ether, wherein particularly the analyte is $K^+$, or
a boronic acid moiety, in particular a boronic acid moiety connected to the polymer via a hydrophobic linker such as a phenyl group, wherein particularly the analyte is glucose.

Regarding the detection of potassium (K) or $K^+$, particularly the polymer Poly(N-isopropylacrylamid) (PNIPAAm) is used in the hydrogel residing in the sensor head's chamber. Here, particularly, the size of the crown ether ring determines which positive ions fit into the respective ring. In principle, regarding crown ether, 1:1 complexes (one crown ether per positive ion, e.g. $K^+$) and 2:1 complexes (two crown ethers per positive ion, e.g. $K^+$) can be used.

Generally any type of crown ether can be used being capable of chelating a specific cation to be detected such as 18-crown-6 or 15-crown-5 ethers. The skilled person is familiar with such terms regarding crown ethers. In a particularly preferred embodiment, the hydrogel of the present invention comprises binding site for 2:1 complexes using two 15-crown-5 moieties. In a further preferred embodiment, a hydrogel is suggested on basis of Poly(N-isopropylacrylamid) (PNIPAAm) being cross-linked and having a plurality of binding sites for 2:1 complexes using two 15-crown-5 moieties.

However, in alternative embodiments, depending on the specific analyte, also other responsive components or compounds can be used, such as one of: Cryptands, spherands, valinomycin, enniatin B, nonactin, gramicidin, FCCP/CCCP, 2,4-dinitrophenol, monensin, ionomycin, podands, cyclodextrins, cyclophanes, calix arenes, resocarene, cavitands, careands, hemicarerands, clefts, tweezers, catenanes and rotaxane.

Particularly cryptands (such as crown ethers) are suitable for metal ions such as $K^+$.

Further, according to an embodiment of the present invention, the crown ether molecules are attached to the hydrogel in such a manner that they form pairs, wherein the two crown ethers of the respective pair are configured to bind an analyte simultaneously, wherein particularly the analyte is arranged between the crown ethers of the respective pair in its bound state (2:1 complex as suggested above).

However, using suitable responsive components/compounds, the invention can be applied to a vast variety of different analytes other than potassium and glucose, particularly the analyte can also be one of the following: Electrolytes, carbohydrates, fatty acids, lipids, sugars, nucleotides, deoxyribonucleic acids, ribonucleic acids, amino acids, peptides, proteins, antibodies, hormones, neuro-transmitters, metabolites, metabolites, antigens, drugs, medicines, nanoparticles, toxins or any other suitable substance known to the person skilled in the art. Further, the analyte can be one of: albumin/globuline, alkaline phosphatase, alpha-1-alpha-1-antitrypsin, alpha-1-fetoprotein, alpha ammonia, antithrombin III, bicarbonate, bilirubin, carbohydrate antigen 19-9, carcino-embryonic antigens, chloride, cholesterol, cholinesterase, chylomicron residues, cobalamin/vitamin B12, coeruloplasmin, C-reactive proteins, Cystatin C, D-dimers, iron, erythropoietin, erythrocytes, ferritin, fetuin A, fibrinogen, folic acid/vitamin B9, free tetraiodothyronine (fT4), free triiodothyronine (fT3), gamma glutamyltransferase, glutamate dehydrogenase, glutamate oxalacetate Transaminase, glutamate pyruvate transaminase, glycohemoglobin, hematocrit, hemoglobin, haptoglobin, uric acid, urea, HDL cholesterol, homocysteine, immunoglobulin A, immunoglobulin E, immunoglobulin G, immunglobulin M, INR, calcium, creatinine, creatine Kinase, copper, lactate, lactate dehydrogenase, LDL cholesterol, leukocytes, lipase, lipoprotein, magnesium, corpuscular hemoglobins, myoglobin, sodium, NT-proBNP/BNP, phosphate, prostate aspergilligen antigens, reticulocytes, rheumafactors, platelets, thyroid stimulant hormone, transferrin, triglycerides, troponin T, and VLDL cholesterol.

Furthermore, generally, the analyte can also be an active substance, wherein the notion active substance shall include typical drugs or metabolites, biologicals, or small molecules comprising, which are given for treatment of diseases such as muscarinic receptor antagonists, neuromuscular blocking agents, cholesterol inhibitors, adrenergic receptor agonists, and indirectly acting sympathomimetic agents, methylxanthines, alpha-adrenergic receptor antagonists, ergot alkaloids, beta-adrenoceptor antagonist, inactivation inhibitors, antisympathotonika, 5-HT receptor agonists, histamine receptor agonists, histamine receptorantagonists, analgesics, local anesthetics, sedatives, anticonvulsants, convulsants, muscle relaxants, Antiparkinsonian agents, neuroleptics, antidepressants, lithium, tranquillizers, immunosuppressants, antirheumatics, antiarrhythmics, antibiotics, ACE inhibitors, aldosterone receptor antagonists, diuretics, vasodilators, positive inotropic agents, antithrombotic/thrombolytic substances, laxatives, antidiarrheals, drugs for obesity, uricostats, uricuricurics, lipid-lowering agents, antidiabetics, antihypoglycaemic agents, hormones, iodine salts, thyrostatic agents, iron, vitamins, trace elements, antivirals, antifungals, antituberkulotics, substances for tumor-brain therapy and vaccines.

Furthermore, according to an embodiment the medium carrying the analyte is a fluid medium, particularly an aqueous medium, particularly one of: a body fluid, blood, lymph, saliva, urine, gastric juice, secretions of the pancreatic bile, sweat, tears of the interstitial fluid, extra cellular fluid, breast milk, vaginal secretion, nasal secretion, ejaculate, menstrual fluid, aqueous humor of the eye, cerebral water, ascites, pleural fluid, pericardial fluid, synovia, amniotic liquor, cerumen and pus.

Furthermore, particularly in case the sensor system according to the invention is applied in the field of environmental/water analysis, analytes may be one of: allergens, plant protectant, pathogens, dioxins, temperature, humidity, conductivity, pH, dissolved oxygen, redox potential, total hardness, carbonate hardness, alkalinity, potential to solve chalk, bromine, chloride, sulfate, sulfite, fluoride, orthophosphate, total phosphorus, cyanide, organic nitrogen, ammonium, nitrate, nitrite, Kjeldahl nitrogen, total nitrogen, total nitrogen bound (TNb), aluminum, antimony, arsenic, barium, beryllium, lead, boron, cadmium, calcium, chromium, cobalt, iron, potassium, copper, magnesium, manganese, molybdenum, sodium, nickel, mercury, sulfur, selenium, silver, tellurium, thallium, titanium, vanadium, Zinc, tin, lithium, TOC, DOC, BODS, COD, permanganate index, phenol total steam, total phenol (phenoline index), AOX, anionic surfactants, nonionic surfactants, lipophilic substances, hydrocarbon index, halogenated hydrocarbons, Mononuclear aromatic hydrocarbons (B, T, X), polychlorinated biphenyls (PCB), polycyclic aromatic hydrocarbons (PAHs), chlorophenols and pesticides (chlorinated pesticides, triazines).

Furthermore, according to an embodiment of the present invention, when the analyte is a metal ion, e.g. K+, the concentration of crown ether in the hydrogel preferably lies within the range from 0 to 40% and most preferably in the range from 3 to 25%.

Furthermore, according to an embodiment of the present invention, when the analyte is glucose, the concentration of the boronic acid moiety in the hydrogel preferably lies within the range from 0 to 45% and most preferably in the range from 4 to 30%.

Furthermore, according to an embodiment, the degree of cross-linking in the hydrogel is adjusted in such a manner that the hydrogel exhibits structural integrity entirely when swollen to the maximum extent. Such a degree of cross-linking has the advantage that the hydrogel is not pressed through the supporting structure of the chamber of the sensor.

Furthermore, according to an embodiment of the present invention, the responsive component or compound is homogeneously distributed in the hydrogel. Alternatively, the distribution of the responsive component may also be inhomogenously in the hydrogel and thus the responsive component resides in concentrated regions.

According to yet another embodiment of the present invention related to the analyte potassium, the hydrogel residing in the chamber comprises a temperature coefficient $K_T=\Delta p/\Delta T$ being the slope of the p-T-curve of the hydrogel (e.g. as measured by the pressure sensor measuring the pressure in the chamber) that lies within the range of 200 mbar/K to 600 mbar/K, and/or a hydrogel $K_{HG}=K_{K+}/K_T$ in the range from 0.001 to 0.2 and most preferably in the range from 0.004 to 0.1. The hydrogel coefficient $K_{HG}$ describes the concentration dependent (left) shift of the p-T-curve.

Particularly, these hydrogel specific parameters can be derived from the p-T-graph associated to the hydrogel residing in the chamber of the sensor head. These parameters can be used to characterize the hydrogel. Also the sensitivity $K_A$ (or $K_{K+}$ in case of K+) can be derived from the p-T-curve. Due to the analyte-dependent shift of the p-T-curve, a pressure change occurs at each given temperature. For instance, in FIG. 6 a pressure reduction of about –400 mbar in the chamber is observed at 28° C. when adding 20 mM $KNO_3$ to the hydrogel (K+ is captured). Consequently, the sensitivity derived therefrom is $K_{K+}$=–400 mbar/20 mM=–20 mbar/mM for the specific hydrogel.

In contrast to a free (isobaric) swelling of the hydrogel, the sensitivity in the isochoric process according to the present invention is essentially constant over broad range of temperatures.

Particularly, according to a preferred embodiment of the present invention, the hydrogel comprises a polymer of the monomer PNIPAAm.

Alternatively, one of the following polymers may be used:
Poly(N-isopropylmethacrylamide) (LCST: 38-42° C.),
Poly(N-ethyl-N-methyl acrylamide) (LCST: 56° C.),
Poly(N,N-diethyl acrylamide) (LCST: 32° C.),
Poly(N,N-dimethylaminoethyl methacrylate) (LCST: 50° C.),
Oligo(ethylenglycol)methacrylate and poly(oligo(ethylene glycol)methacrylate) (LCST: 26-90° C.).

Particularly, according to an embodiment of the present invention, the hydrogel comprises a network comprising a plurality of cross-linked polymer chains wherein a plurality of non-cross linked (e.g. linear) polymer chains are bound to the network, wherein only the non-cross-linked polymer chains comprise the responsive component/compound. Particularly, according to an embodiment, the molar fraction of the responsive compound within the respective non-cross linked polymer chain is in the region between 30-70%, particularly 50%.

Furthermore, according to a preferred embodiment of the present invention, the sensor system comprises an analyzing unit that is configured to determine the presence or concentration of the analyte using at least the pressure measured in the chamber of the sensor head of the sensor by means of the pressure sensor.

Furthermore, according to a preferred embodiment of the present invention, the sensor system further comprises a telemetry unit that is configured to wirelessly transfer the measured pressure to the (e.g. remote) analyzing unit.

Furthermore, according to preferred embodiment of the present invention, the sensor head (and particularly also further sensors or reference sensors of the sensor system) is configured to be implantable into a human or animal body.

Further, according to preferred embodiment of the present invention, for reducing a cross-sensitivity of the sensor, the sensor system comprises at least one reference sensor which comprises a reference hydrogel, which corresponds to the hydrogel in the chamber of the sensor, but without the responsive components (such that the reference sensor/reference hydrogel has the same or at least a similar cross-sensitivity with respect to salts and the same or at least a similar temperature dependence as the hydrogel in the chamber of the sensor). Particularly, also the reference sensor may comprise a sensor head having a chamber filled with the reference hydrogel and a pressure sensor for measuring a reference pressure in the chamber of the reference sensor. Particularly, the analyzing unit is configured to compensate/correct the pressure measured in the chamber of the sensor with the reference pressure. The difference of both pressures eliminates cross-sensitivity.

Here, the invention makes use of the surprising findings according to which the effects of the components of the hydrogel with respect to the measured pressure of the reference hydrogel are additive also in complex solutions (e.g. cell culture medium). This eases compensation of cross-sensitivities of e.g. potassium sensitive hydrogels by use of a reference sensor.

Particularly, the reference sensor may be used to determine disturbances/cross-sensitivities such as e.g. ion concentration, temperature dependence and aging of the hydrogel/polymer network due to degrading processes.

According to an embodiment, the sensor system may comprise a further second sensor sensitive to another analyte, say analyte B, in contrast to analyte A detected by the (first) sensor. The second sensor may also use a thermoresponsive hydrogel. Here, the sensor system may comprise a further (second) reference sensor that is configured to determine cross-sensitivities with respect to the second sensor. This may also be used to determine/eliminate cross sensitivities concerning the first sensor and analyte B and the second sensor and analyte A. Particularly, the sensor system may comprise an arbitrary number of sensors and corresponding reference sensors.

Particularly, according to an embodiment, the sensor and the at least one reference sensor may comprise the same hydrogel, wherein now the sensor head of the reference sensor is not permeable for the analyte. Particularly, a pore size of the permeable area (e.g. switchable membrane) of the sensor head of the reference sensor is selected such that the analyte cannot pass the permeable area. Possible degradation processes and cross sensitivities occur in both sensors. During idle times when no pressure measurements are taken place the permeable areas are preferably closed.

Furthermore, also the reference sensor may comprise a telemetry unit for transmitting the measured reference pressure to the analyzing unit. However, the reference sensor may also use the telemetry unit of the sensor (e.g. common telemetry unit).

Furthermore, according to preferred embodiment of the sensor system according to the present invention, the sensor system comprises a temperature sensor and/or a separate pressure sensor (without a hydrogel) in order to sample further data for reducing cross sensitivities, particularly for compensating blood pressure variations.

Further, according to preferred embodiment of the sensor system according to the present invention, the sensor system comprises an external pressure sensor for reducing the influence of external barometric pressure changes (e.g. in an ambient atmosphere surrounding it is the patient into whom the sensor head and particularly the at least one reference sensor are implanted).

The barometric pressure sensor can be integrated into an external patient device or into an external therapy device. Furthermore, the barometric pressure sensor may be integrated into an external device (e.g. patient or therapy device) that also comprises the analyzing unit to which pressure data is sent by the telemetry unit of the sensor.

Set external device can be configured to be linked to the sensor (e.g. implanted into the patient) via communication connection, particularly a wireless communication connection, for instance a radio communication connection. Here, the measured barometric pressure can be simultaneously detected and offset with the pressure measured by the sensor in the chamber of the sensor.

Furthermore, according to yet another embodiment of the present invention, the sensor of the sensor system comprises a component which is configured to mechanically decouple a change in the pressure of the hydrogel in the chamber resulting from a change in temperature of the hydrogel from the concentration dependent pressure measured by the pressure sensor of the sensor.

Particularly, for this, the pressure sensor may be arranged in the compartment separated from the chamber by a flexible pressure membrane (e.g. bellows, polymer film) to which the hydrogel residing in the chamber is coupled. Particularly the compartment may be filled with a material (e.g. a fluid), such as an oil, which material comprises a positive temperature coefficient and particularly functions as a compensation component. In contrast thereto, the hydrogel comprises a negative temperature coefficient. In case the hydrogels temperature increases, the hydrogel shrinks whereas the material arranged in the compartment expands. Particularly, the amount of the material is selected such, that the increase in volume of the material with temperature exactly or at least partly compensates the temperature induced decreasing volume of the hydrogel.

Further, according to yet another aspect of the present invention, a method for detecting or determining the concentration of an analyte in a medium is disclosed, wherein a sensor system according to the present invention is used for detecting the presence or concentration of the analyte.

Other features which are considered as characteristic for the invention are set forth in the appended claims.

Although the invention is illustrated and described herein as embodied in a sensor system for detecting the presence or concentration of analytes, it is nevertheless not intended to be limited to the details shown, since various modifications and structural changes may be made therein without departing from the spirit of the invention and within the scope and range of equivalents of the claims.

The construction and method of operation of the invention, however, together with additional objects and advantages thereof will be best understood from the following description of specific embodiments when read in connection with the accompanying drawings.

DETAILED DESCRIPTION OF THE INVENTION

Figure 2:
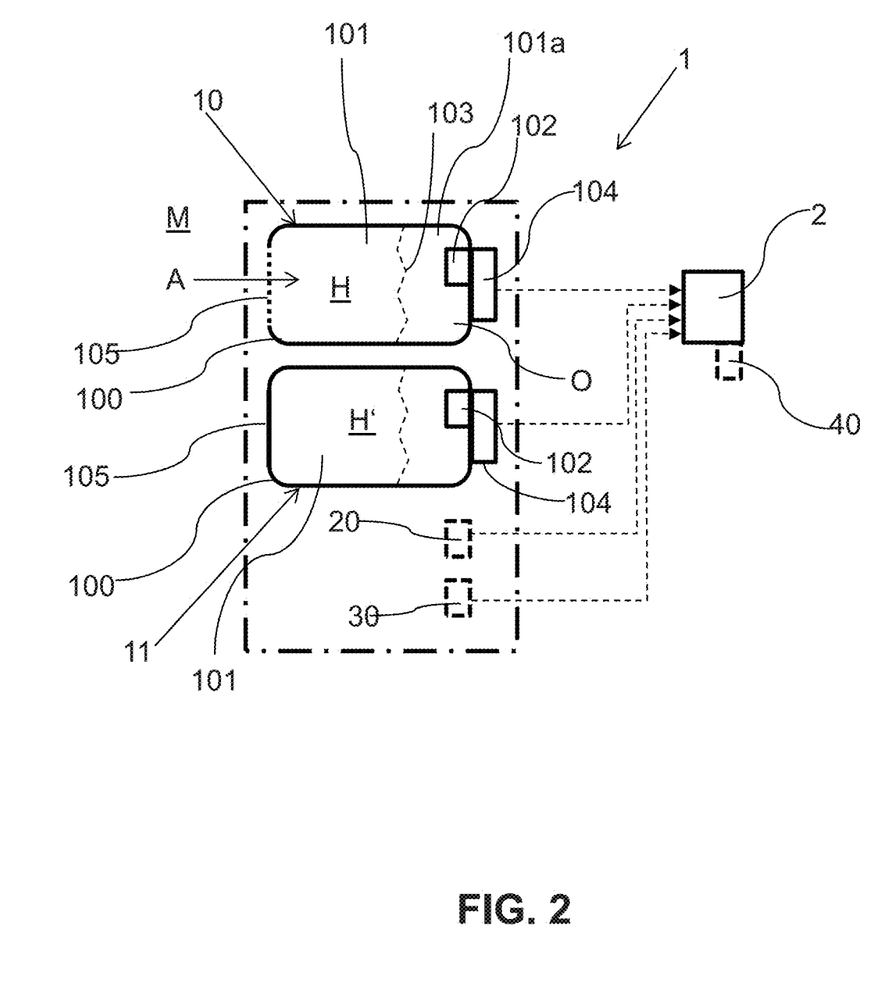
FIG. 2 is a schematic illustration of a sensor system according to the invention.

Referring now to the figures of the drawings in detail and first, particularly to FIG. 2 thereof, there is shown a schematic representation of a sensor system 1 according to the present invention. As indicated in FIG. 2, the sensor system 1 comprises for detecting the presence or concentration of an analyte A in a medium M at least an (e.g. implantable) sensor 10 having an sensor head 100 enclosing a chamber 101, which sensor head 100 further comprises a permeable area 105 through which the analyte A can pass into the chamber 101 when the sensor head 100 contacts the medium M.

Further, the sensor 10 comprises a cross-linked hydrogel H filling the chamber 101, which hydrogel H is configured to undergo a change in volume when contacting the analyte A passed into the chamber 101 which leads to a change in pressure in the chamber (101), and a pressure sensor 102 configured to measure the pressure P in the chamber 101 for detecting the presence or concentration of the analyte A.

Particularly, as indicated in FIG. 1, the hydrogel H comprises a lower critical solution temperature LCST, which decreases (from LCSTb to LCSTa) when the analyte A, here K$^+$, bonds to the hydrogel H and which increases when the analyte A is released from the hydrogel H.

Figure 3:
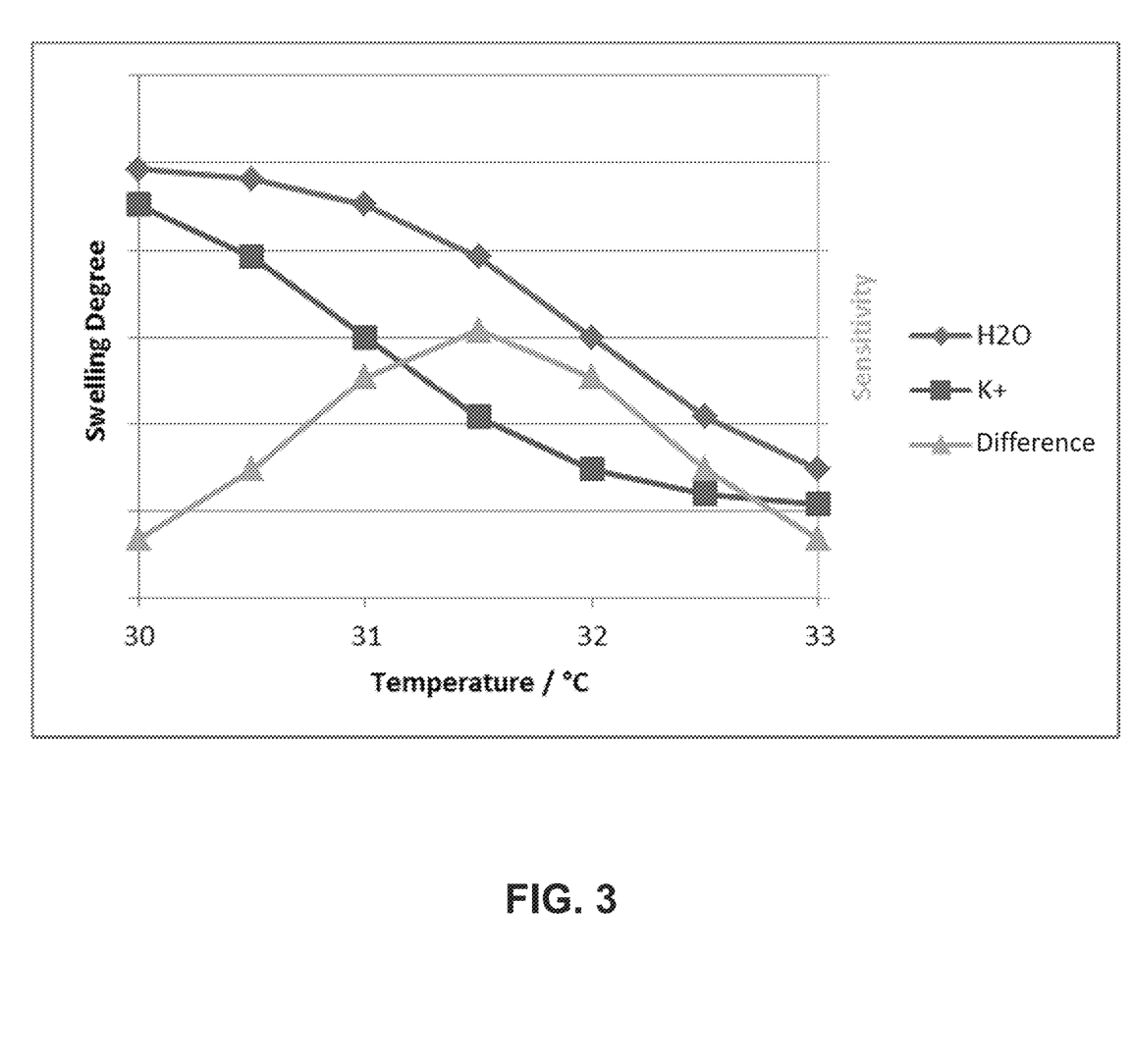
FIG. 3 is a graph showing a 2:1 crown ether complex (responsive compound for capturing metal ions, particularly K$^+$)
Figure 4:
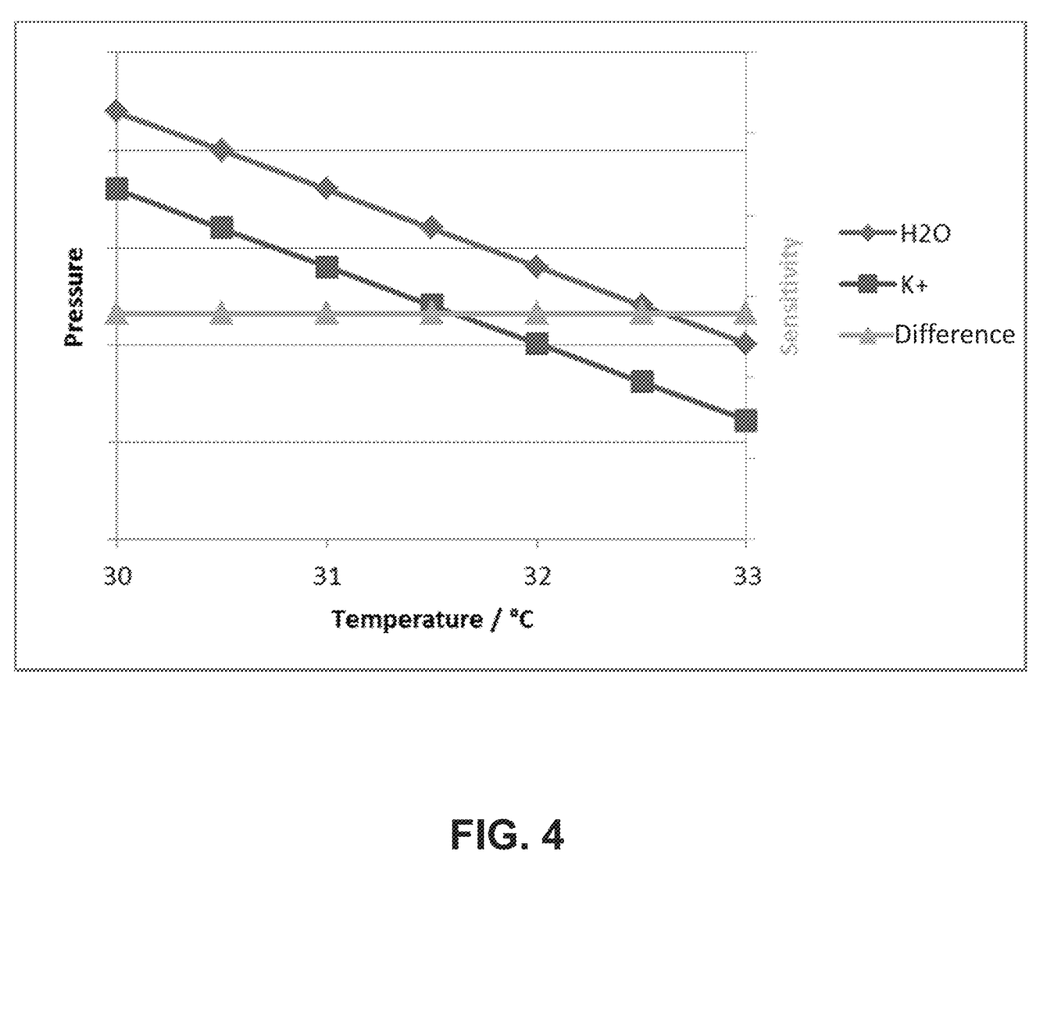
FIG. 4 is a graph showing different polymer structures of a hydrogel that can be used with the present invention: (A), (B), (C), (D), (E)
Figure 5:
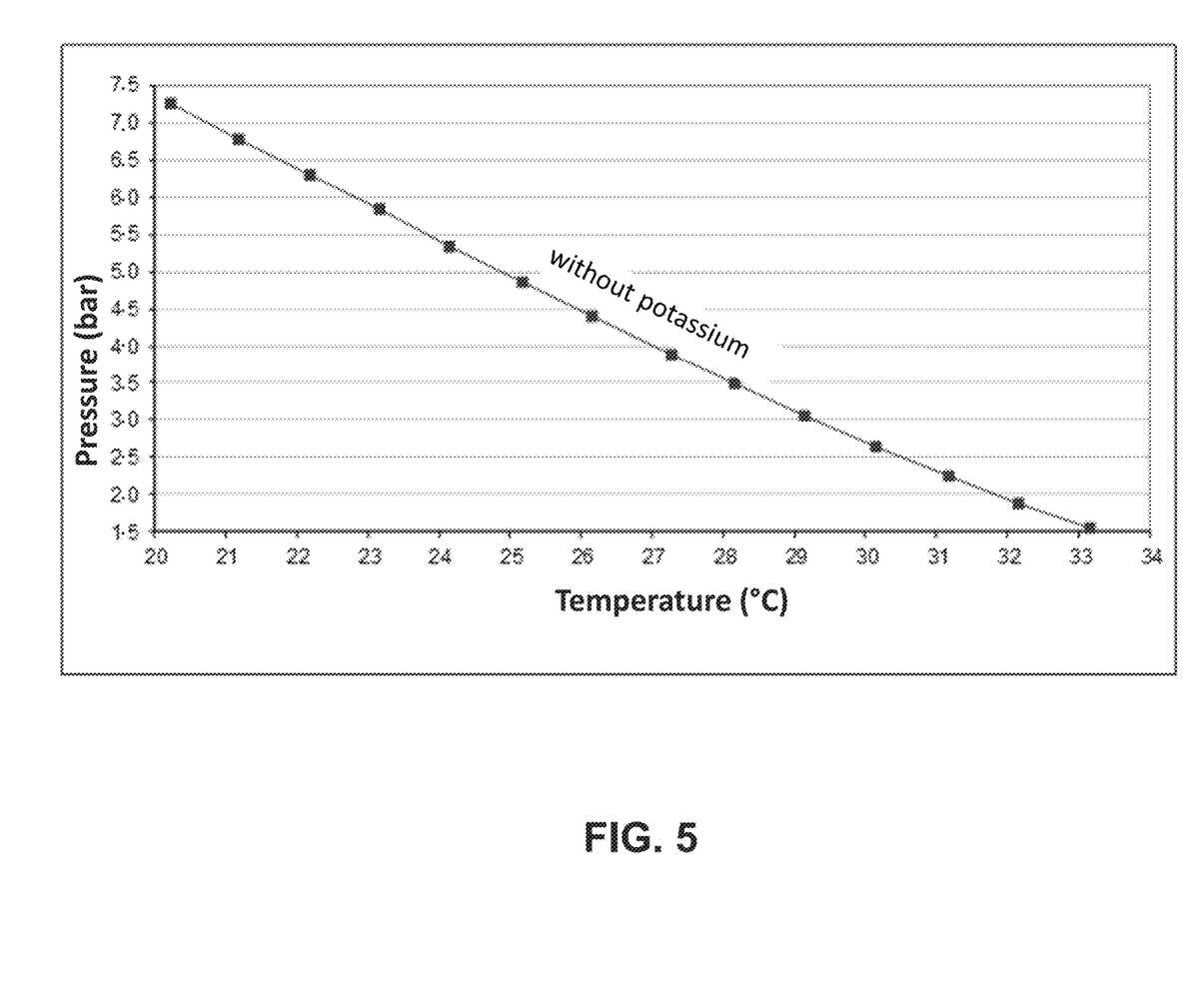
FIG. 5 is a graph showing a P-T-curve (e.g. measured pressure over temperature) of an isochoric hydrogel according to the present invention (without analyte)

However, due to the fact that the hydrogel H according to the present invention is kept in an isochoric state in the chamber 101, the pressure measured in the chamber by a pressure sensor 102 surprisingly depends essentially linearly (and/or mildly quadratically) on the temperature of the hydrogel H in the chamber 101 as indicated in FIG. 4, which leads to a constant sensitivity of the sensor 10 for the analyte A, here K+, over a broad range of temperatures. In contrast thereto, FIG. 3 shows the sigmoidal curves (swelling degree vs. temperature for free swelling which result in case of isobaric measurements that disadvantageously comprise a rather small measuring window of only a few degrees in temperature.

Figure 6:
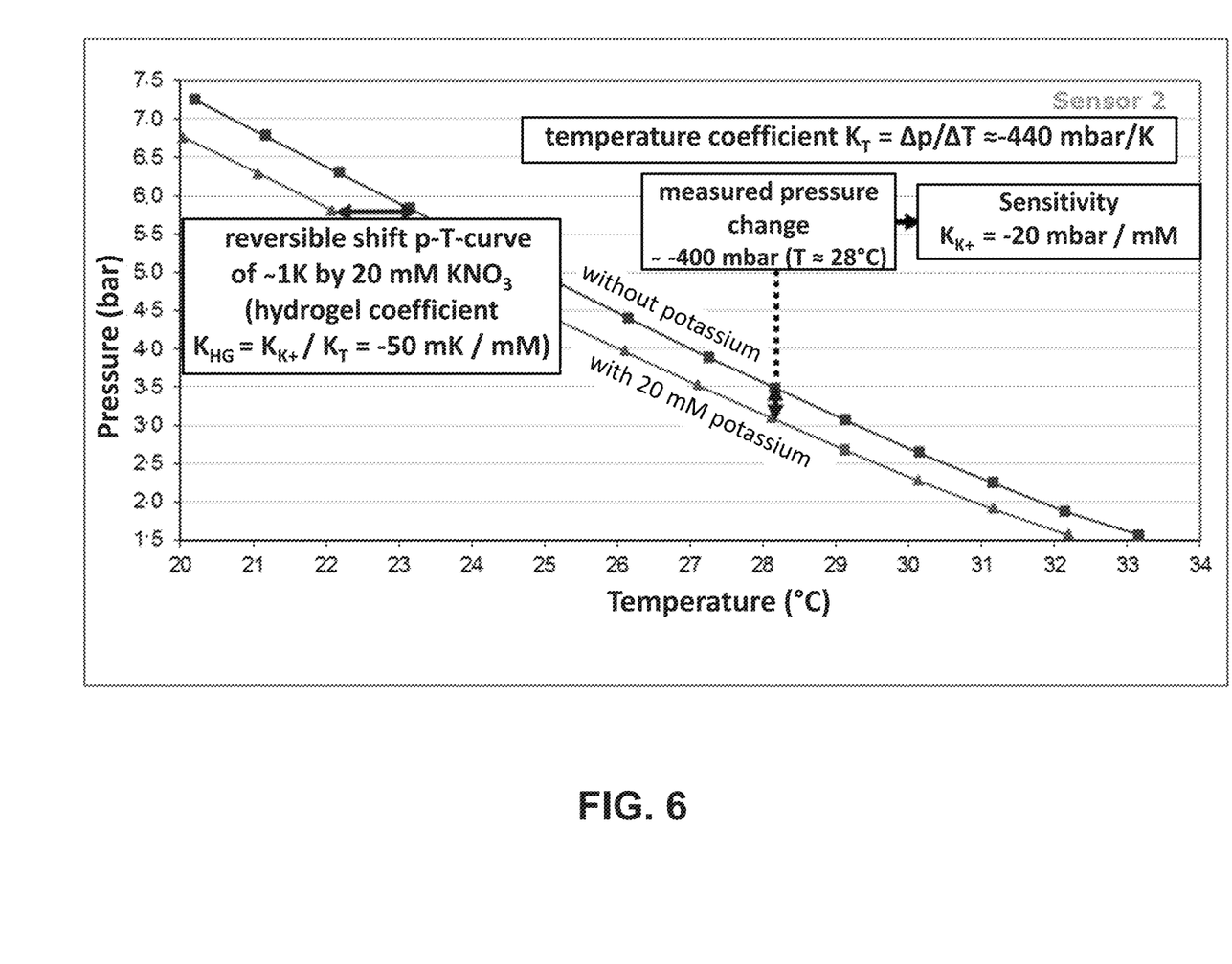
FIG. 6 is a graph showing hydrogel specific parameters as derived from the P-T-curve of the isochoric hydrogel.

The hydrogel H according to the invention can be characterized by the following parameters that can be derived from the pressure-temperature curve (P-T curve) as shown in FIG. 6.

The first of these parameters is the temperature coefficient $K_T = \Delta p/\Delta T$ which is the slope of the (isochoric) P-T-curve of the hydrogel H measured by pressure sensor 102 that preferably lies within the range of 200 mbar/K to 600 mbar/K.

A further characteristic parameter is the sensitivity for the respective analyte (here e.g. K+) which is denoted as $K_{K+}$. As indicated in FIG. 6, the latter quantity can also be easily derived from the P-T-curve. Due to the potassium-dependent shift of the P-T-curve, a pressure change occurs at each given temperature. For instance, in FIG. 6 a pressure reduction of about −400 mbar occurs in the chamber 101 at 28° C. due to adding of 20 mM KNO$_3$ to the hydrogel H. Thus, the corresponding sensitivity is $K_{K+}$=−400 mbar/20 mM=−20 mbar/mM for the hydrogel N residing in chamber 101.

A third parameter is the so called hydrogel coefficient, which is defined as $K_{HG}=K_{K+}/K_T$ and described the concentration dependent (left) shift of the p-T-curve. Preferably $K_{HG}=K_{K+}/KT$ lies in the range from 0.001 to 0.2 and most preferably in the range from 0.004 to 0.1.

In contrast to a free (isobaric) swelling of the hydrogel (see FIG. 3), the sensitivity in the isochoric process according to the present invention is essentially constant over a broad range of temperatures as can be seen from FIGS. 4 and 6.

Figure 7:
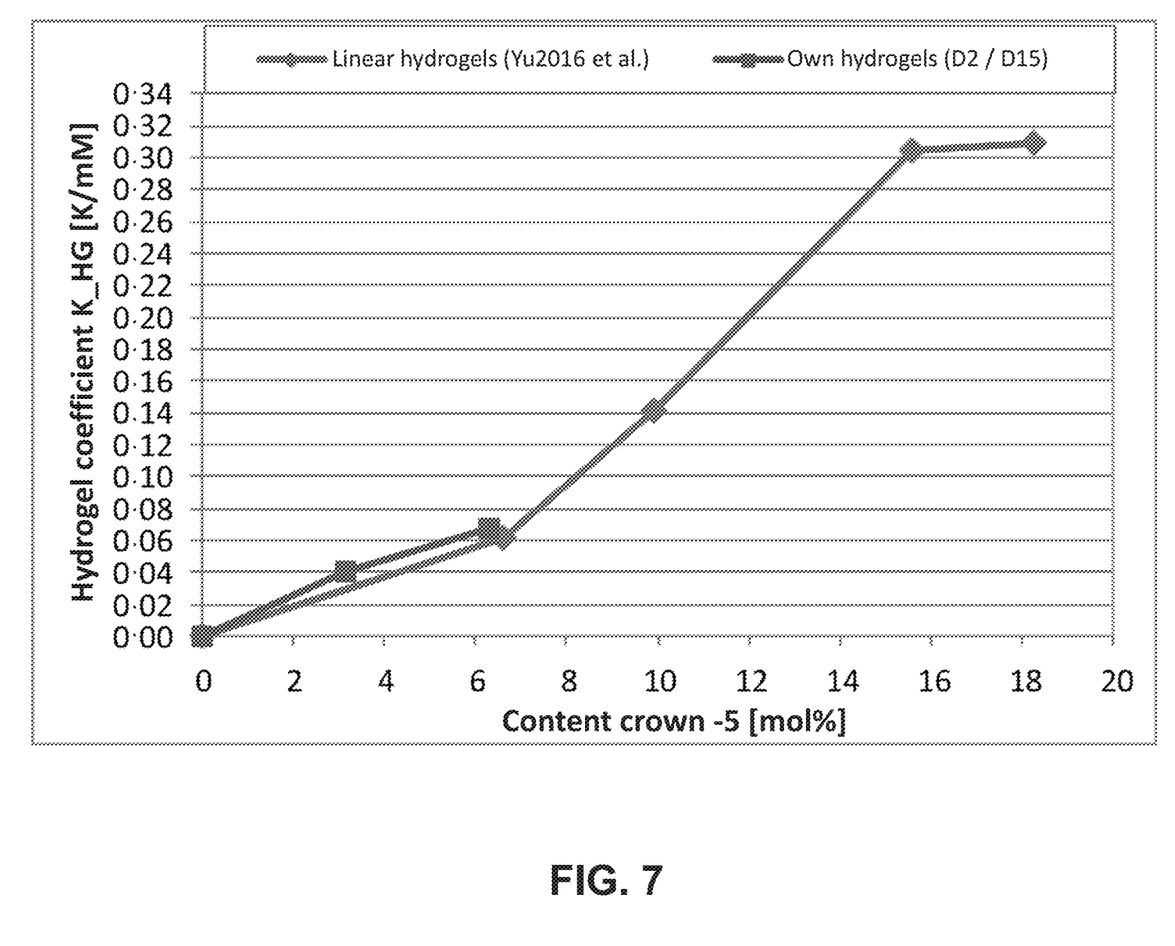
FIG. 7 is a graph showing a is a graph showing hydrogel coefficient for a cross-linked hydrogel (squares) in comparison to linear hydrogels (diamonds)

Furthermore, so far, only linear 2:1 hydrogels have been discussed which comprise depending on potassium concentration a high sensitivity in a narrow temperature region. However, until now, for the cross-linked variants high sensitivities have not been observed. The high sensitivities of the linear polymers are possible due to a high fraction of crown ether in the respective polymer, particularly—depending on the crown ether fraction—the hydrogel coefficient $K_{HG}$ can be increased by increasing the crown ether fraction in the linear hydrogel, i.e., in case of a fraction of 15 mol-% a coefficient $K_{HG}$ being larger than 0.3 K/mM is observed (see FIG. 7), which corresponds to a shift of the swelling degree temperature curve of more than 6 K when adding 20 mM KNO$_3$ in water.

Surprisingly, the hydrogel coefficients KHG for the linear and cross-linked hydrogels correlate very well (see FIG. 7), wherein the sole parameter seems to be the crown ether fraction. This is intriguing since the detection of potassium in a 2:1 complex two crown ethers are required. The original assumption according to which linear hydrogels can fold more easily than 3D cross-linked polymers so that the crown ethers can come more easily in close proximity can thus not be verified. However, in case of cross-linked hydrogels an increase of the crown ether fraction is not easily possible without further ado, since the relatively large crown ether monomers disturb the cross-linking sterically.

Adapting the synthesis accordingly, cross-linked hydrogels having a crown ether fraction of 10% could be generated.

Suitable hydrogels can be prepared according to the following exemplary procedure.

The monomers of N-isopropylacrylamid, acrylamide and 4-acrylamidobenzo-15-crown-5 (B15C5Am) as well as the cross-linking agent N,N'-methylen-bis(acrylic acid amide) (MBAAM) were solved in KNO$_3$ solution in a vial equipped septum and magnetic stir bar, degassed for 15 minutes upon argon supply and cooled to 15° C. Subsequently a enhancing agent tetramethylethylenediamine (TEMED) and an initiator (ammonium persulfate, APS) were added to the KNO$_3$ solution and the resulting solution is degassed for about 90 sec. Thereafter the reaction solution is transferred quickly to argon flooded reactor. After reacting for 24 hours at 15° C. the resulting hydrogel is washed with water (MilliQ water) up to 6 times.

In order to significantly increase the fraction of crown ether, the following strategies can be applied.

Figure 8:
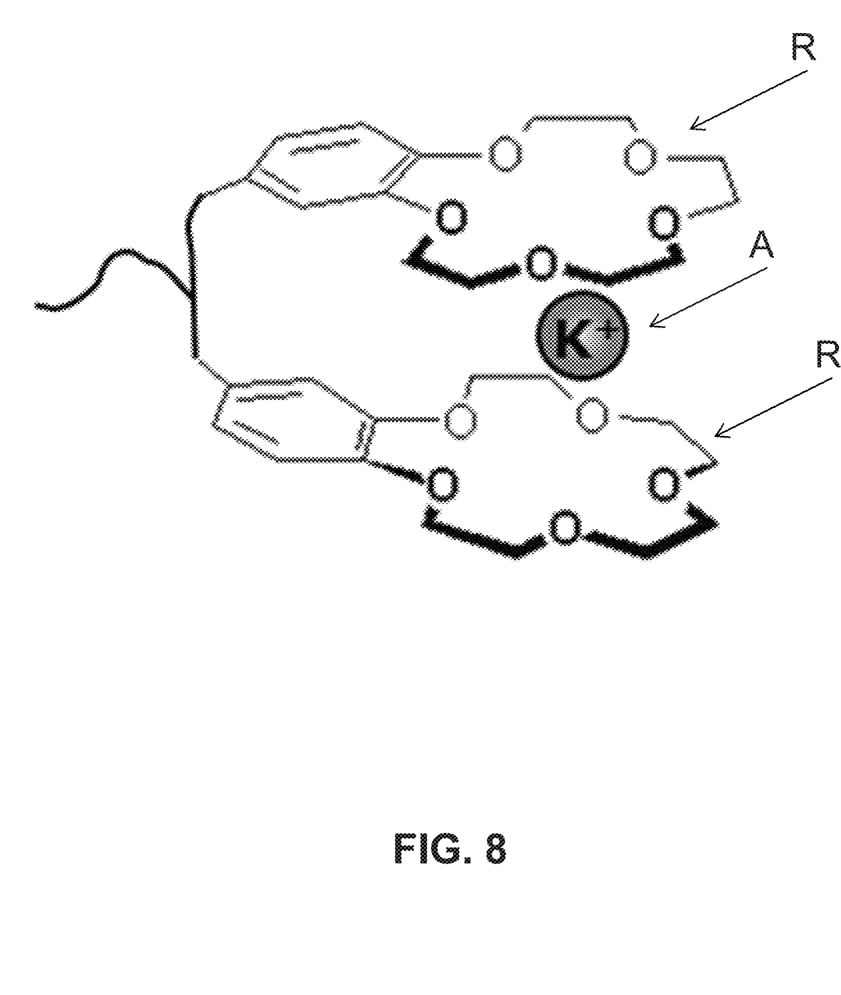
FIG. 8 is an illustration of a preferred configuration of crown ether in a cross-linked hydrogel according to the present invention for capturing metal ions, particularly K$^+$.

As indicated in FIG. 8, here in case of the analyte A in form of $K^+$, the H of the sensor system 1 comprises a plurality of a responsive component R, here crown ether, wherein the respective responsive component R is responsive to the analyte A such that the volume of the hydrogel H tends to decrease when the respective responsive component R binds to the analyte A such that the pressure P in the chamber 101 decreases, and wherein the volume of the hydrogel H tends to increase when an analyte A is released from the respective responsive component R. Particularly, as indicated in FIG. 8, the crown ether molecules R are attached such to the hydrogel H that they form pairs, particularly in a chelation configuration, wherein the two crown ethers of the respective pair are configured to bind the analyte A simultaneously, wherein particularly the analyte A is arranged between the crown ethers of the respective pair in its bound state, as shown in FIG. 8. Particularly, the two crown ethers can be generated in the chelation configuration before the actual hydrogel synthesis. The configuration of crown ethers shown in FIG. 8 is also denoted as pincer structure.

For this, the two crown ethers are spatially and covalently bonded in the form of the pincer by using suitable synthesis parameters. This allows an easy increase of the crown ether amount by a factor of two. Furthermore, the crown ethers are already positioned in close proximity for the potassium detection, so that a reaction due a changing potassium concentration can take place much faster than using a conventional approach, since polymer chains do not have to be re-oriented for finding potassium due to the crown ether sandwich.

Figure 9A:
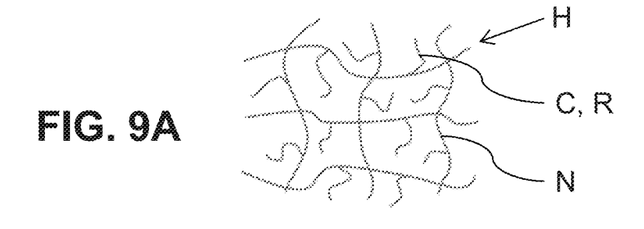
FIGS. 9A-9E are illustrations showing different possible structures ((A) to (E)) of a hydrogel according to the present invention.

Further, according to an embodiment indicated in FIG. 9A, the crown ether fraction may be enhanced by providing a hydrogel H that comprises a network N, e.g. a PNIPAAm network, comprising a plurality of cross-linked polymer chains wherein a plurality of non-cross linked polymer chains C is bound to the network N (and distributed over the network), wherein only the non-cross-linked (e.g. linear) polymer chains C comprise the responsive component R (e.g. the crown ether structure). The molar fraction of crown ether in the non-cross linked (e.g. linear) chains preferably lies in the range about 40 to 60% and is preferably approximately 50%. Particularly, a free radical polymerization can be used for producing this special hydrogel, in which the individual components are distributed inhomogeneously in the network in a defined manner. Particularly a PNIPAAm network without crown ethers can be provided, in which linear (non-cross-linked) areas with high crown ether fraction are incorporated by polymerization.

Alternatively, the PNIPAAm network N may comprise a high fraction of crown ether. The linear (non-cross linked) areas can be configured as before.

Figure 9B:
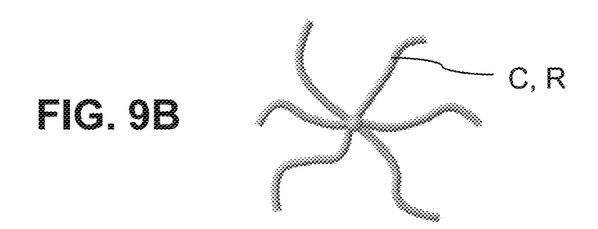
Figure 9C:
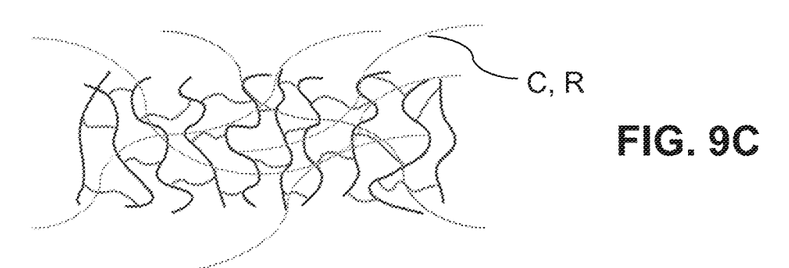
Figure 9D:
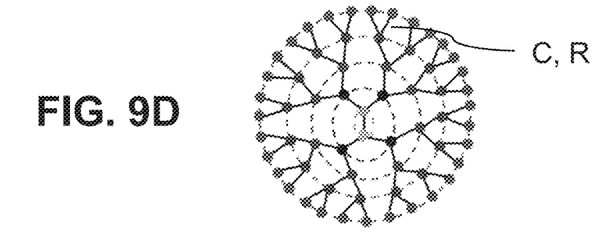
Figure 9E:
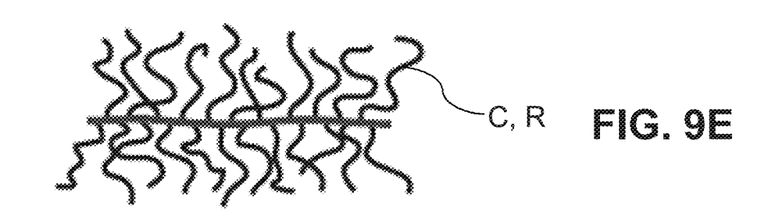

The generation of the linear regions C with a high crown ether fraction in the hydrogel H can also be achieved by configuring the polymer of the hydrogel H as a star polymer (see FIG. 9B), as a dendrimer (see FIG. 9D), as a blend (see FIG. 9 C), or as a copolymer, particularly as a graft polymer or toothbrush-like polymer (see FIG. 9E).

As an alternative to the free radical polymerization also strategies for a controlled radical polymerization can be used (e.g. NMP, ATRP, RAFT).

As also indicated in FIG. 2, the sensor system 1 may comprise further components.

Particularly, in an embodiment, the sensor system 1 further comprises an analyzing unit 2 that is configured to determine the presence or concentration of the respective analyte A using the measured pressure P.

Preferably, for transmitting the measured pressures P to the unit 2, preferably wirelessly, the sensor 10 may comprises a telemetry unit 104 that communicates with the analyzing unit 2.

This allows to implant the sensor 10 into a patient, while the analyzing unit can be arranged outside the patient.

Furthermore, for reducing cross-sensitivity of the sensor 10, the sensor system 1 may comprise at least one reference sensor 11 that comprises a reference hydrogel H'. The reference hydrogel H' can be identical to the hydrogel H wherein now the analyte A is not allowed to enter the chamber 101 of the sensor head 100 of the reference sensor 11. For this the reference sensor 11 may comprise a suitable area 105 or no such area at all. Alternatively, the reference hydrogel H may be configured as the hydrogel H, but does not comprise the responsive component R so that a change in analyte concentration in the chamber 101 of the reference sensor 11 does not affect the reference pressure measured by the pressure sensor 102 of the reference sensor.

Preferably, the analyzing unit 2 is configured to offset the pressure measured in the chamber 101 of the sensor 10 against the reference pressure measured by the pressure sensor 102 of the reference sensor 11.

Particularly, in an embodiment, the sensor system 1 may comprise multiple sensors 10, which may be identically configured, with the exception that each sensor 10 comprises a hydrogel that is sensitive to a different analyte. Further, such a system 1 may comprise a corresponding number of reference sensors 11 to reduce/eliminate cross-sensitivities and other disturbances.

For further reduction of such cross-sensitivities and disturbances, the sensor system may further comprise a separate temperature sensor 20 and/or pressure sensor 30 that may also communicate with the analyzing unit 2.

Furthermore, the sensor system may comprise an external pressure sensor 40 for reducing the influence of external barometric pressure changes on the pressure measurements in the sensors 10 and/or 11.

Finally, as indicated in FIG. 2, each sensor 10, 11 or individual sensors of the system 1 may optionally comprise a component 103, O which mechanically decouples a change in the pressure of the hydrogel H, H' in the respective chamber 101 resulting from a change in temperature of the hydrogel H from the concentration dependent pressure P measured by the respective pressure sensor 102. Particularly, the respective pressure sensor 102 may be arranged in compartment 101a separated from the chamber 101 by a flexible pressure membrane (e.g. bellows, polymer film) 103 to which the hydrogel H residing in the respective chamber 101 is mechanically coupled (e.g. contacts the pressure membrane 103). Particularly, the respective compartment 101a may be filled with a material (e.g. a fluid), such as an oil O, which material O comprises a positive temperature coefficient and particularly functions as a compensation component. In contrast thereto, the hydrogel H (H') comprises a negative temperature coefficient. In case the hydrogel's H temperature increases, the hydrogel H shrinks, whereas the material O arranged in the compartment 101a expands. Particularly, the amount of the material O is selected such that the increase in volume of the material O with temperature exactly or at least partly compensates the temperature induced decreasing volume of the hydrogel.

The invention claimed is:

1. A sensor system for detecting a presence or concentration of an analyte in a medium, the sensor system comprising:
   a sensor having a sensor head with a chamber, said sensor head having a permeable area through which the analyte can pass into said chamber when said sensor head contacts the medium;
   a cross-linked hydrogel filling said chamber, said cross-linked hydrogel being configured to undergo a change in volume when contacting the analyte passed into said chamber which leads to a change in pressure in said chamber, said cross-linked hydrogel having a plurality of a responsive component, said responsive component being responsive to the analyte such that the volume of said cross-linked hydrogel decreases when said responsive component binds to the analyte such that the pressure in said chamber decreases, and the volume of said cross-linked hydrogel increases when the analyte is released from said responsive component such that the pressure in said chamber increases, said responsive component comprising a crown ether; and
   a pressure sensor configured to measure the pressure in said chamber for detecting the presence or the concentration of the analyte, wherein said cross-linked hydrogel is in isochoric condition in said chamber and has a generally linear dependency of a measured pressure for temperatures of said cross-linked hydrogel below a lower critical solution temperature,
   wherein molecules of said crown ether are attached to said cross-linked hydrogel such that they form pairs of said crown ether molecules, wherein two of said crown ethers of a respective pair of molecules are configured to bind the analyte simultaneously, and wherein the analyte is disposed between said crown ethers of the respective pair of molecules in a bound state.

2. The sensor system according to claim 1, wherein said cross-linked hydrogel comprises at least one of:
   a temperature coefficient $KT=\Delta p/\Delta T$ being a slope of a Pressure-Temperature-curve of said cross-linked hydrogel, the temperature coefficient KT lying within a range of 200 mbar/K to 600 mbar/K; and
   a hydrogel coefficient $KHG=KK+/KT$ in a range from 0.001 to 0.2.

3. The sensor system according to claim 1, wherein said cross-linked hydrogel comprises a polymer of one of a monomer selected from the group consisting of N-isopropylmethacrylamide, N-ethyl-N-methyl acrylamide, N,N-diethyl acrylamide, N,N-dimethylaminoethyl methacrylate, and (ethylenglycol)methacrylate.

4. The sensor system according to claim 1, wherein said cross-linked hydrogel has a network with a plurality of cross-linked polymer chains and a plurality of non-cross-linked polymer chains bound to said network, and only said non-cross-linked polymer chains contain the responsive component.

5. The sensor system according to claim 1, wherein said sensor contains an analyzer configured to determine the presence or the concentration of the analyte using a measured pressure.

6. The sensor system according to claim 5, wherein said sensor contains a telemeter configured to transfer the measured pressure to said analyzer.

7. The sensor system according to claim 1, further comprising:
   at least one reference sensor having a reference hydrogel for reducing cross-sensitivity of said sensor, said reference sensor further having a reference sensor head with a reference chamber filled with said reference hydrogel and a reference pressure sensor for measuring a reference pressure in said reference chamber of said reference sensor; and
   an analyzer configured to correct a pressure measured in said chamber of said sensor with or by subtracting the reference pressure.

8. The sensor system according to claim 1, wherein said sensor contains a component which mechanically decouples a change in the pressure of said cross-linked hydrogel in said chamber resulting from a change in temperature of said cross-linked hydrogel from an analyte concentration dependent pressure measured by said pressure sensor of said sensor.

9. The sensor system according to claim 1, wherein said responsive component is configured to detect K+ as the analyte.

10. The sensor system according to claim 1, wherein said responsive component achieves a linear dependency between temperature and pressure irrespective if the analyte is present or not.

11. The sensor system according to claim 1, wherein said cross-linked hydrogel contains a Poly(N-isopropylacrylamid) having at least 20 mol-% of said crown ether chemically bonded to polymer chains.

12. The sensor system according to claim 1, wherein said crown ether is 15-crown-5.

* * * * *